US012576017B2

(12) United States Patent
Russell et al.

(10) Patent No.: US 12,576,017 B2
(45) Date of Patent: Mar. 17, 2026

(54) SUNSCREEN COMPOSITION WITH ENHANCED PHOTOPROTECTION

(71) Applicant: Edgewell Personal Care Brands, LLC, Chesterfield, MO (US)

(72) Inventors: Michael Russell, Madison, NJ (US); Daniel Torri, Morristown, NJ (US)

(73) Assignee: Edgewell Personal Care Brands, LLC, Chesterfield, MO (US)

( * ) Notice: Subject to any disclaimer, the term of this patent is extended or adjusted under 35 U.S.C. 154(b) by 15 days.

(21) Appl. No.: 17/906,795

(22) PCT Filed: Sep. 23, 2021

(86) PCT No.: PCT/US2021/051707

§ 371 (c)(1),
(2) Date: Sep. 20, 2022

(87) PCT Pub. No.: WO2022/260691

PCT Pub. Date: Dec. 15, 2022

(65) Prior Publication Data

US 2024/0207152 A1 Jun. 27, 2024

Related U.S. Application Data

(60) Provisional application No. 63/208,761, filed on Jun. 9, 2021.

(51) Int. Cl.

| | |
|---|---|
| ***A61K 8/14*** | (2006.01) |
| ***A61K 8/02*** | (2006.01) |
| ***A61K 8/35*** | (2006.01) |
| ***A61K 8/37*** | (2006.01) |
| ***A61K 8/40*** | (2006.01) |
| ***A61K 8/81*** | (2006.01) |
| ***A61K 8/9789*** | (2017.01) |
| ***A61Q 17/04*** | (2006.01) |

(52) U.S. Cl.

CPC .............. *A61K 8/35* (2013.01); *A61K 8/0291* (2013.01); *A61K 8/37* (2013.01); *A61K 8/40* (2013.01); *A61K 8/8152* (2013.01); *A61K 8/9789* (2017.08); *A61Q 17/04* (2013.01)

(58) Field of Classification Search

None

See application file for complete search history.

(56) References Cited

U.S. PATENT DOCUMENTS

| | | | | |
|---|---|---|---|---|
| 2006/0067896 | A1* | 3/2006 | Schaffer | A61Q 17/04 424/59 |
| 2008/0181858 | A1* | 7/2008 | Davis | A61K 8/87 424/59 |
| 2015/0216782 | A1* | 8/2015 | Britze | A61K 8/40 424/59 |
| 2019/0105248 | A1* | 4/2019 | Yang | A61K 8/14 |
| 2021/0093529 | A1 | 4/2021 | LaRosa et al. | |

FOREIGN PATENT DOCUMENTS

| | | | |
|---|---|---|---|
| EP | 3315116 | A1 | 5/2018 |
| GB | 2438047 | A | 11/2007 |
| WO | 2004/110366 | A2 | 12/2004 |

OTHER PUBLICATIONS

International Preliminary Report on Patentability mailed on Dec. 21, 2023 in International Application PCT/US2021/051707.

Search Report and Written Opinion issued in connection with corresponding PCT Application No. PCT/US2021/051707 dated Feb. 28, 2022.

Anonymous, "Classic Body Sunscreen SPF 70", Database GNP MINTEL; XP055893347, May 6, 2021.

Unofficial translation of the Office Action issued by the Mexican Institute for Industrial Property (IMPI) on Feb. 4, 2025, in Mexican Patent Application No. MX/a/2022/011466.

* cited by examiner

*Primary Examiner* — Brian Gulledge

(74) *Attorney, Agent, or Firm* — Edgar Rodriguez

(57) ABSTRACT

A sunscreen composition includes a sunscreen active, a carrier, and a film former polymer. The sunscreen active may be selected from organic sunscreen actives. The carrier may include an amphiphile monolayer to encapsulate a least a portion of the total amount of the sunscreen active. The film former polymer may include an acrylic film former polymer selected from $C_1$-$C_{30}$ alkyl (meth)acrylates copolymer. Notably, the sunscreen active may provide enhanced photoprotection at relatively low concentration levels when present with the carrier, including the amphiphile monolayer, and the acrylic film former polymer.

18 Claims, 2 Drawing Sheets

Reference Example 1

Reference Example 2

Example 1

SUNSCREEN COMPOSITION WITH ENHANCED PHOTOPROTECTION

CROSS-REFERENCE TO RELATED APPLICATIONS

This application claims priority to International Application No. PCT/US2021/051707, filed Sep. 23, 2021, which claims priority to U.S. Provisional Patent Application No. 63/208,761, filed on Jun. 9, 2021, the contents of which are incorporated herein by reference in their entirety.

TECHNICAL FIELD

Embodiments relate to sunscreen compositions including a sunscreen active and a synergistic combination of a carrier, having an amphiphile monolayer to encapsulate at least a portion of the total amount of the sunscreen active, and a film former polymer.

BACKGROUND

Ultraviolet (UV) solar radiation falling within the UVA region (320 nm to 400 nm) is damaging owing to its ability to reach deeper into the dermis layer as compared to UV solar radiation falling within the UVB region (290 nm to 320 nm). As such, UVA radiation may suppress immune function, lead to loss of skin elasticity, promote premature signs of aging, or lead to other undesirable health effects. Meanwhile, UVB radiation is absorbed by the epidermis layer to cause erythema and cellular mutations that damage the skin or underlying tissue. Indeed, the erythemal action spectrum reveals that 99% of erythemal action resides in the UVB region and 1% resides in the UVA region. Thus, sunscreen compositions are available to protect keratinous substrates, such as skin and hair, from UV radiation.

A measure of UVA protection provided by a sunscreen composition, the UVA Protection Factor (UVAPF), and of UVB protection, the Sun Protection Factor (SPF), may reliably be determined in vitro and in vivo using traditional spectroscopic analysis techniques. Such testing traditionally demonstrates that the amount of UV protection is proportional to an amount of UV active in a sunscreen composition. For example, a sunscreen composition may have organic UV actives present in an amount of more than 30.0 wt. % to provide an SPF≥50. Relatively high amounts of UV actives, however, can increase the cost of a sunscreen composition and/or augment technical challenges related to its application or performance.

Ingredients, such as boosters, may be used to augment UV protection. Nonetheless, using relatively high amounts boosters to provide relatively high SPF values (e.g., SPF 50) can increase the cost of a sunscreen composition and/or, augment technical challenges related to its application or performance. Thus, there is considerable room for improvement to provide a sunscreen composition having enhanced photoprotection using less ingredients and/or ingredients such as a UV active, film former, and carrier at relatively lower amounts.

SUMMARY

Embodiments relate to sunscreen compositions including a sunscreen active, a carrier, and a film former polymer. In embodiments, the sunscreen active may include a physical sunscreen active, an organic sunscreen active, or combinations thereof. For example, the sunscreen active may include only organic sunscreen active(s). Meanwhile, the carrier may include an amphiphile monolayer to encapsulate at least some of the sunscreen active. For example, the carrier may encapsulate 50% to more of the active.

The film former polymer may include at least one acrylic film former polymer. In one example, the acrylic film former polymer may be selected from $C_{1-30}$ alkyl (meth)acrylates copolymer. Preferably, the film former polymer has a molecular weight of 1,500,000 Daltons or less, more preferably 1,500,000 Daltons or less, more preferably 500,000 Daltons or less, more preferably 300,000 Daltons or less such as, for example, about 10,000 Daltons to about 300,000 Daltons, including every number and/or fraction therebetween.

Notably, a sunscreen composition may provide enhanced photoprotection using fewer total ingredients and/or ingredients at relatively lower concentration levels. For example, low concentration levels of sunscreen active(s), carrier(s), and/or film former polymer(s) may be used. In one example, a sunscreen active may be present in an amount of greater than zero and less than 30.0 wt. %, based on the total weight of the composition, to provide an SPF of, e.g., ≥50 when present with a carrier and a film former. In addition, as discussed in detail below, relatively low amounts of film former polymer and/or carrier may be used to achieve the desired SPF. Moreover, no booster may be necessary and/or used.

Optionally, however, a photoprotection booster may be added. In one example, a photoprotection booster includes a carbohydrate selected from maize starch, potato starch, wheat starch, rice starch, cassava starch, tapioca starch, barley starch, or combinations thereof. In one example, the photoprotection booster includes *Zea* Maize starch. The photoprotection booster may be present in an amount, for example, greater than zero and less than or equal to about 7.5 wt. %, based on the total weight of the composition.

In any of the preceding embodiments, the carrier may form a micelle via an amphiphile monolayer to at least partly encapsulate a sunscreen active. In one example, the carrier includes *Carthamus Tinctorius* oleosomes, *Prunus Amygdalus Dulcis* oleosomes, or combinations thereof. The carrier may be present in an amount, for example, greater than zero and less than or equal to about 15.0 wt. %, based on the total weight of the composition.

In any of the preceding embodiments, the film former polymer may be selected from alkyl (meth)acrylates copolymers. In one example, the film former polymer may be selected from $C_{1-30}$ alkyl (meth)acrylates copolymer, such as acrylates/$C_{12}$-$C_{22}$ alkyl methacrylate copolymer. The film former polymer may be dissolved in a solvent such as, without limitation, a non-aqueous solvent. For example, the film former polymer may be dissolved in isododecane, isohexadacane, diisopropyl adipate, isoparaffin, alcohol, organosilicon compound, or combinations thereof. The film former polymer may also be dissolved in water. The film former polymer may be present in an amount, for example, greater than zero and less than or equal to about 5.0 wt. %, based on the total weight of the composition.

Embodiments further relate to a method to protect a keratinous surface from UV radiation including contacting the keratinous surface with the sunscreen composition of any of the preceding embodiments. Embodiments further relate to a method to manufacture a sunscreen composition of any the preceding embodiments, comprising at least mixing a sunscreen active, a carrier, and a film former polymer. In one example, heating may be conducted between about 40° C. and about 60° C. to form the sunscreen composition. Embodiments further relate to a consumer packaged product including the sunscreen composition of any of the preceding embodiments.

BRIEF DESCRIPTION OF THE DRAWINGS

The features of the disclosure believed to be novel and the elements characteristic of the invention are set forth with particularity in the appended claims. The figures are for illustration purposes only and are not drawn to scale. The disclosure itself, however, both as to organization and method of operation, can best be understood by reference to the description of the preferred embodiment(s) which follows, taken in conjunction with the accompanying drawings in which:

DETAILED DESCRIPTION

Figure 1:
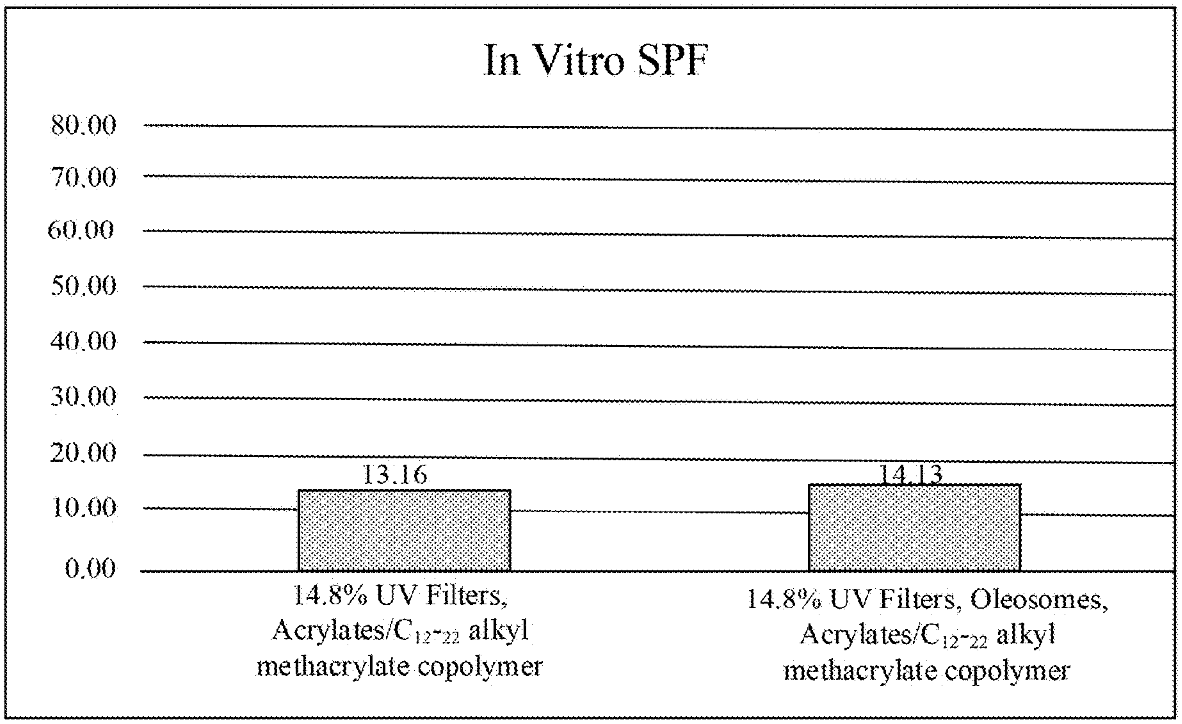
FIG. 1 is a graph showing sun protection factor (SPF) performance in vitro for sunscreen compositions including a sunscreen active, a film former polymer, with and without a carrier, screened for photoprotection performance according to embodiments.

Embodiments can comprise, consist of, and consist essentially of the features and/or steps described herein, as well as any of the additional or optional ingredients, components, steps, or features described herein or would otherwise be appreciated by one of skill in the art. It is to be understood that all concentrations disclosed herein are by weight percent (wt. %.) based on a total weight of the composition unless otherwise indicated. Where appropriate, the International Nomenclature of Cosmetic Ingredients (INCI) name of ingredients/components is provided. Any numerical range recited herein is intended to include all sub-ranges subsumed therein, and such ranges are understood to include each and every number and/or fraction between the stated range lower and upper values. Moreover, the term "about" may refer to deviations of ±20%.

Sunscreen Active(s)

A sunscreen composition includes a sunscreen active capable of substantially absorbing, scattering, and/or deflecting UV radiation on a keratinous substrate. Preferably, the sun protection factor (SPF) of a sunscreen composition is ≥8 and the UVA protection factor (UVAPF) is at least ⅓ the SPF. Thus, for example, physical or mineral sunscreen actives include metal oxides (e.g., titanium dioxide, zinc oxide, combinations thereof, etc.) that may be used in effective amounts to provide an SPF of 8 or more (in contrast to other uses as colorants, etc.). Such filters may have various morphologies such as crystalline form (e.g., rutile, etc.), size (e.g., nano, non-nano, etc.), shape (e.g., amorphous, spherical, etc.), and functionalization (e.g., coatings, etc.) that allow for the effective use as sunscreen actives.

A sunscreen active may preferably include an organic sunscreen active such as, for example, p-aminobenzoic acid (PABA) and derivatives thereof, avobenzone (also known as butylmethoxy dibenzoylmethane), 2,4-dihydroxybenzophenone, 2,2',4,4'-tetrahydroxybenzophenone, oxybenzone, sulisobenzone, sulisobenzone sodium, 2,2'-dihydroxy-4,4'-dimethoxybenzophenone, 5-chloro-2-hydroxybenzophenone, dioxybenzone, sodium 2,2'-dihydroxy-4,4'-dimethoxybenzophenone-5,5'-disulfonate, 2-hydroxy-4-methoxy-4'-methyl-benzophenone, octabenzone, ethyl dihydroxypropyl-p-aminobenzoate, glyceryl-p-aminobenzoate, homosalate, methyl anthranilate, octocrylene, octyl dimethyl-p-aminobenzoate, isoamyl-p-methoxycinnamate, octyl methoxycinnamate, octyl salicylate, triethanolamine salicylate, 3-(4-methylbenzylidene) camphor, enzacamene, phenylbenzimidazole sulfonic acid, methylene bis-benzotriazolyl tetramethylbutyl phenol, 4-isopropyldibenzoylmethane, octisalate, bis-ethylhexyloxyphenol methoxyphenyl triazine, 4-isopropyl-dibenzoylmethane, terephthalylidene dicamphor sulfonic acid (also known as ecamsule), drometrizole trisiloxane, diethylhexylbutamido triazone, ethylhexyl triazone, cinoxate, ensulizole, bis-disulizole disodium, diethylamino hydroxybenzoyl hexylbenzoate, or combinations thereof.

A sunscreen active that provides protection against UVA radiation may include avobenzone, terephthalylidene dicamphor sulfonic acid, bis-disulizole disodium, disodium phenyl dibenzimidazole tetrasulfonate, diethylamino hydroxybenzoyl hexylbenzoate, bis-diethylamino hydroxybenzoyl benzoate, bis-benzoxazolylphenyl ethylhexylamino triazine, or combinations thereof. A sunscreen active that provides protection against UVB radiation may include octocrylene, octinoxate, octisalate, homosalate, ensulizole, ethylhexyl triazone, enzacamene, amiloxate, diethylhexyl butamido triazine, benzylidene malonate polysiloxane, padimate-O, trolamine salicylate, cinoxate, PABA, or combinations thereof. A sunscreen active that provides protection against UVA and UVB radiation may include oxybenzone, meradimate, titanium dioxide, zinc oxide, bis-octrizole, bemotrizinol, drometrizole trisiloxane, sulisobenzone, dioxybenzone, or combinations thereof. A sunscreen active that provides protection against damaging radiation within other regions in the electromagnetic spectrum, such as blue light (380 nm to 500 nm), may include, without limitation, metal oxides (e.g., titanium dioxide, zinc oxide, combinations thereof, etc.).

A sunscreen active may be selected based on an ability of, and/or operation to, substantially absorb, scatter, and/or deflect UV radiation on a keratinous substrate. Additionally or alternatively, a sunscreen active may be selected based on an affinity for an aqueous phase and/or a lipid phase. For example, the partition coefficient (P) may be used to determine the propensity of a neutral (uncharged) compound to dissolve in an immiscible biphasic system of lipid (fats, oils, organic solvents) and water. Thus, a sunscreen active may be selected based on a determination of a negative value for log P indicating a higher affinity for the aqueous phase (more hydrophilic) or a positive value for log P indicating a higher affinity for the lipid phase (more lipophilic). Table I, reproduced from J. Soc. Cosmetic Chem., 38, 209-221, Table V, July/August 1987, illustrates example log P values for sunscreen actives.

TABLE 1

| CTFA name | Other names | Log P @25° C. |
|---|---|---|
| Glyceryl PABA | 1,2,3-Propanetriol,1-(4-aminobenzoate) | −0.02 |
| Benzophenone-4 | Sulisobenzone | −1.51 |
| PABA | p-Amino benzoic acid | 0.74 |
| Benzophenone-8 | Dioxybenzone | 2.15 |
| Cinoxate | Ethoxyethyl methoxy cinnamate | 2.55 |
| Benzophenone-3 | Oxybenzone | 2.63 |
| Ethyl dihydroxypropyl PABA | Ethyl-4-bis(2-hydroxypropyl-aminobenzoate) | 2.84 |

TABLE 1-continued

| CTFA name | Other names | Log P @25° C. |
|---|---|---|
| Amyl dimethyl PABA | Amyl dimethyl PABA | 4.53 |
| Butylmethoxy dibenzoylmethane | Butylmethoxy dibenzoylmethane | 4.86 |
| Menthyl anthranilate | Menthyl-O aminobenzoate | 5.05 |
| Octyl salicylate | 2-Ethylhexyl salicylate | 5.30 |
| Homosalate | Homomenthyl salicylate | 5.61 |
| Octyl methoxy cinnamate | Ethylhexyl-p-methoxy cinnamate | 5.65 |
| Octocrylene | Octyl cyanodiphenylacrylate | 5.69 |
| Octyl dimethyl PABA | 2-Ethylhexyl-p-dimethyl aminobenzoate | 6.08 |

A sunscreen active may be present in a lower amount, to provide a same or higher SPF and/or UVAPF value, compared to an amount of that sunscreen active in traditional sunscreen compositions. A sunscreen active may, for example, be present in an amount of about 1.0 wt. % to less than 30.0 wt. %, based on the total weight of the sunscreen composition. For example, a sunscreen active may be present in an amount of 0.8 wt. %, 1.0 wt. %, 2.0 wt. %, 3.0 wt. %, 4.0 wt. %, 5.0 wt. %, 6.0 wt. %, 7.0 wt. %, 8.0 wt. %, 9.0 wt. %, 10.0 wt. %, 15.0 wt. %, 20.0 wt. %, 25.0 wt. %, 29.9 wt. %, including every number and/or fraction therebetween, based on the total weight of the sunscreen composition.

In one example, a sunscreen composition includes a sunscreen active present in an amount of about 15.0 wt. %, such as in an amount of 13.5 wt. %, 15.0 wt. %, 18.0 wt. %, including every number and/or fraction therebetween, based on the total weight of the sunscreen composition. For example, a sunscreen composition may include avobenzone, octocrylene, homosalate, and octisalate in a total amount≤about 15 wt. %, based on the total weight of the sunscreen composition, to provide an SPF of ≥50. A sunscreen composition may include avobenzone (e.g., Parasol® 1789), diethylamino hydroxybenzoyl hexyl benzoate (e.g., Uvinul® A Plus), ethylhexyl triazone (e.g., Uvinul® T150), bemotrizinol (e.g., Uvasorb® HEB), and/or bis-ethylhexyloxyphenol methoxyphenyl triazine (Tinosorb® S), e.g., in a total amount less than 30.0 wt. %, such as ≤20 wt. %, or more preferably ≤15 wt. %, based on the total weight of the sunscreen composition, to provide an SPF≥8, for example ≥15, ≥30, ≥50, and so on. In addition, a sunscreen composition may exclude (e.g., be free of) benzophenone-3, octyl methoxycinnamate, 2-ethylhexyl-2-cyano-3,3-diphenylacrylate, 3,3,5-trimethylcyclohexyl salicylate, and/or 2-ethylhexyl salicylate.

Carrier(s)

A sunscreen composition includes a carrier having an amphiphile monolayer to at least partly encapsulate a sunscreen active. In one example, the amphiphile monolayer may encapsulate more than 90%, preferably more than 99%, of a total amount of sunscreen active present in the sunscreen composition. Generally, amphiphiles are molecules with a head group having ionic, polar, and/or hydrogen-bond-forming chemical groups that render them relatively soluble in water (hydrophilic) and a tail group having saturated and/or unsaturated hydrocarbon chains that render them relatively insoluble in water (hydrophobic). An amphiphile may include, for example, lipid molecules such as phospholipids having a hydrophilic head group attached to a hydrocarbon chain tail.

Amphiphiles assemble into structures at a critical micelle concentration (CMC). Amphiphiles may, for example, assemble into micelles having an amphiphile monolayer at the interface of an immiscible biphasic system (e.g., O/W, W/O, etc.). For example, amphiphiles with relatively small tail groups and relatively large head groups, or head groups with a large effective size such as ionically charged groups, may form micelles in water with hydrophobic tails providing a core surrounded by a hydrophilic shell. Micelles may be substantially spherical or ellipsoidal, or may form other configurations such as substantially cylindrical and reversed phase with hydrophilic tails forming a core surrounded by a hydrophobic shell. Thus, micelles may encapsulate oil-soluble sunscreen actives (e.g., log P>1), such as octocrylene, avobenzone, phenyl salicylate, etc., among the lipophilic tails thereof and/or may encapsulate water soluble sunscreen actives (e.g., log P<1), such as glycryl PABA, benzophenone-4, etc., among the aqueous tails thereof.

Preferably, a carrier includes natural-based micelles. Oleosome (oil bodies), for example, are types of micelles derived from plant tissues including seeds, roots, and leaves of plants, although oleosomes may be most abundant from seeds and nuts. Oleosomes may have a diameter of up to a few microns, such as in a range of about 0.2 μm to about 2.0 μm. The core of an oleosome may include triacylglycerols (TAGs) and the shell may include a mixture of a phospholipid monolayer and anchored (interfacial) proteins such as oleosins, caleosins, and steroleosins. The phospholipid monolayer may include, for example, ionic groups with phosphatidylcholine (PC) and/or phorphatidylserine (PS) tail groups that can provide a shell thickness of about 0.9 nm at the interface of an immiscible biphasic system.

Oleosomes selected from *Carthamus Tinctorius* oleosomes and *Prunus Amygdalus Dulcis* oleosomes are available in aqueous dispersions under the tradename Capsol® and Hydresia® by Botaneco, Inc. For example, an oleosome suspension may be at a pH range of 3.5 to 5.0, at a viscosity of 500 cps to 2400 cps (DVE Viscometer, LV-3 @5.0 rpm for 30 seconds at ambient temperature), at an oleosome to oil ratio between 1:1 and 1:3, and/or at a % oleosome solids content of 55 wt. % to 70 wt. %, based on the total weight of the oleosome suspension. Embodiments may not require each oleosome or any oleosome to be coated with a solid material including, for example, acrylate nano latex, fumed silica, cetyl silica silylate, zeolite, natural clay, synthetic clay, ethyl cellulose, micro-crystalline cellulose, cyclodextrin, vegetable protein, sodium caseinate, inulin lauryl carbamate, sodium octenyl-25 succinate starch, or sodium octenylsuccinate phytoglycogen.

Aqueous dispersions of oil bodies include, for example, *Carthamus Tinctorius* (Safflower) Oleosomes (and) Water available under the tradename Capsol™ consisting of a mixture of 56.8 wt. % to 65.5 wt. % vegetable oil, protein, and phospholipids, 1.4 wt. % to 1.6 wt. % D-glucono-1,5-lactone, 0.4 wt. % to 0.6 wt. % sodium benzoate, 0.8 wt. % to 0.9 wt. % citric acid, 0.9 wt. % to 1.1 wt. % sodium hydroxide (Ion), and 31.0 wt. % to 39.0 wt. % water. *Carthamus Tinctorius* (Safflower) Oleosomes (and) Water is available under the tradename Hydresia® SF2 consisting of a mixture of 59 wt. % to 67 wt. % vegetable oil, protein, and phospholipids, 1.5 wt. %, D-glucono-1,5-Lactone, 0.5 wt. % sodium benzoate, and 31 wt. % to 30 wt. % water. *Carthamus Tinctorius* (Safflower) Oleosomes (and) Glycerin (and) Water is available under the tradename Hydresia® G2 consisting of a mixture of 55 wt. % to 63 wt. % vegetable oil, protein, and phospholipids, 20 wt. % glycerin 20.00, 0.75 wt. % D-glucono-1,5-Lactone, 0.25 wt. % sodium benzoate, and 16 wt. % to 24 wt. % water. *Prunus Amygdalus Dulcis* (Sweet Almond) Oleosomes (and) Glycerin (and) Water is available under the tradename Hydresia®

Dulcé consisting of a mixture of 55 wt. % to 63 wt. % vegetable oil, protein, and phospholipids, 20 wt. % glycerin 20.00, 0.75 wt. % D-glucono-1,5-lactone, 0.25 wt. % sodium benzoate, and 16 wt. % to 24 wt. % water. Such oleosomes may load up to 30% of their weight in oil-soluble actives and solubilize water-soluble actives in anhydrous compositions. Mixtures of such dispersions may provide tailored ingredient quantities.

A carrier may be present in an amount of about 1.0 wt. % to about 15.0 wt. %, based on the total weight of the sunscreen composition. A carrier may, for example, be present in an amount of 0.8 wt. %, 1.0 wt. %, 5.0 wt. %, 10.0 wt. %, 15.0 wt. %. 18.0 wt. %, including every number and/or fraction therebetween, based on the total weight of the sunscreen composition. For example, a sunscreen composition may include a dispersion composed of *Carthamus tinctorius* (Safflower) Oleosomes available under the tradename Capsol™ in an amount s about 10.0 wt. %, or for example 5 about 6.55 wt. %, based on the total weight of the sunscreen composition.

Film Former Polymer(s)

A sunscreen composition includes a film former polymer capable of providing a substantially homogenous and/or structured hydro-lipidic film on skin owing to its viscosity-building properties. Generally, a film former polymer may be synthesized from two or more different monomers to form copolymers and/or may from individual polymer chains that are connected by bridging molecules or cross-linking agents to form crosslinked copolymers known as cross polymers. Notably, however, certain cross polymers may primarily or exclusively provide gelling, rheology modifier, binder, absorbent, or hair fixative functionality owing to their structure and/or activation. For example, single molecules of carbomers have a molecular weight of 500,000+ Daltons which when crosslinked increases to over 1 billion Daltons to thicken at marked degrees. Preferably, the film former polymer has a molecular weight of 1,500,000 Daltons or less, more preferably 500,000 Daltons or less, more preferably 300,000 Daltons or less such as, for example, about 10,000 Daltons to about 300,000 Daltons. Thus, the film former may include an acrylic film former polymer such as, without limitation, acrylates/$C_{12-22}$ alkyl methacrylate copolymer (300,000 Daltons) alone or in combination with one or more other film formers having a molecular weight of 1,500,000 Daltons or less.

A film former polymer may be present in a non-aqueous solvent such as, for example, an alcohol, an ether, a fatty acid, a silicone fluid, an ester, a hydrocarbon, a fluorinated hydrocarbon, or combinations thereof. In one example, a film former polymer is dissolved in isododecane, isohexadacane, diisopropyl adipate, isoparaffins (e.g., $C_{13}$-$C_{16}$ isoparaffins), alcohol (e.g., $C_2$-$C_{10}$ alcohols, etc.), organosilicon compounds (e.g., disiloxane, dimethicone, cyclopentasiloxane, etc.), or combinations thereof. A film former polymer may be present in an aqueous solvent, for example dispersed in water. In some embodiments, an acrylic film former polymer may be present in a percent solids content of about 20 wt. % to 100 wt. %, for example 30 wt. % to 40 wt. % when admixed with a dispersant, based on the total weight of the mixture.

An acrylic film former polymer may be selected from acrylates copolymers, which can be prepared from acrylic acid monomers, methacrylic acid monomers, the alkyl esters thereof, and/or the salts thereof. Acrylates copolymers may have the general structure of formula (I):

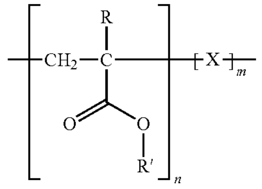

(I)

where R is hydrogen or methyl; R' is hydrogen or an alkyl group such as methyl, ethyl, propyl, butyl, etc., or a salt cation (e.g., sodium); and X is one or more co-monomer residues.

Acrylates copolymers may also include, for example, acrylate esters of different alkoxyl or polyalkoxyl groups (e.g., polyethylene oxide, etc.) with the general structure of formula (II):

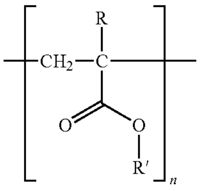

(II)

where R is hydrogen or methyl; and R' is alkoxyl or polyalkoxyl (e.g., polyethylene glycol (PEG)-n, where n=integer such as 23, etc.).

Acrylates copolymers preferably include $C_{1-30}$ alkyl (meth)acrylate copolymers such as, without limitation, $C_{6-14}$ perfluoroalkylethyl acrylate/HEMA copolymer (e.g., SR Polymer) available by Daikin Industries, Ltd., $C_{8-22}$ alkyl acrylates/methacrylic acid crosspolymer (e.g., Intelimer®) available by Air Products and Chemicals, Inc., $C_{12-16}$ alkyl PEG-7 methacrylate/perfluorohexylethyl methacrylate copolymer (e.g., Silkrom HB 27) available by Giovanni Bozzetto SpA, acrylates/$C_{12-22}$ alkyl methacrylate copolymer (e.g., Alliance OPT) available by ISP Technologies, acrylates/$C_{5-8}$ alkyl acrylate copolymer, or combinations thereof. Embodiments may, however, include at least one cross polymer as a rheology modifier agent and require at least one film former polymer having a molecular weight of 1,500,000 Daltons or less, preferably 1,000,000 Daltons or less, or optionally be free of a rheology modifier agent such as acrylates/$C_{10-30}$ alkyl acrylate cross polymer.

A film former polymer may be present in an amount of about 0.1 wt. % to about 5.0 wt. %, based on the total weight of the sunscreen composition. A film former polymer may, for example, be present in an amount of 0.08 wt. %, 0.9 wt. %, 1.0 wt. %, 2.5 wt. %, 5.0 wt. %, 6.0 wt. %, including every number and/or fraction therebetween, based on the total weight of the sunscreen composition. For example, a sunscreen composition may include a dispersion composed of acrylates/$C_{12-22}$ alkyl methacrylate copolymer present in an amount≤about 2.5 wt. %, based on the total weight of the sunscreen composition.

Other Ingredient(s)

A sunscreen composition may include other ingredients such as, without limitation, added water, additional film formers, cosmetically acceptable carriers, oils, sterols, amino acids, moisturizers, powders, colorants, pigments, dyes, pH adjusters, fragrances, cosmetic active ingredients, vitamins, preservatives, preservative boosters, foaming agents, chelating agents, cleansers, essential fatty acids, sphingolipids, self-tanning compounds, fillers, emulsifiers, antioxidants, surfactants, additional film formers, chelating agents, gelling agents, thickeners, emollients, humectants, minerals, viscosity and/or rheology modifiers, keratolytics, retinoids, hormonal compounds, alpha-keto acids, anti-mycobacterial agents, anti-fungal agents, anti-microbials, anti-virals, analgesics, anti-allergenic agents, H1 or H2 antihistamines, anti-inflammatory agents, anti-irritants, anti-neoplastics, immune system boosting agents, immune system suppressing agents, anti-acne agents, anesthetics, antiseptics, insect repellents, skin cooling compounds, skin protectants; skin penetration enhancers, exfoliants, lubricants, staining agents, depigmenting agents, hypopigmenting agents, stabilizers, pharmaceutical agents, photostabilizing agents, spherical powders, extracts (fruit, flower, plant), absorbents, salicylic acid, alpha and beta hydroxy acids, retinol and its derivatives, or combinations thereof.

One or more other ingredients may be present in an amount of about 0.2 wt. % to about 98.0 wt. %, based on the total weight of the sunscreen composition. One or more other ingredients may, for example, be present in an amount of 0.18 wt. %, 2.0 wt. %, 5.0 wt. %, 50.0 wt. %, 98.5 wt. %, including every number and/or fraction therebetween, based on the total weight of the sunscreen composition. For example, a sunscreen composition may include phenoxyethanol, chlorphenesin, caprylyl glycol, dipropylene glycol dibenzoate, glycerin, ammonium acryloyldimethyltaurate/VP copolymer, xanthan gum, and sodium hydroxide, present in an amount of ≥about 50 wt. %, based on the total weight of the sunscreen composition. A photoprotection booster may be present in an amount of 0.45 wt. %, 1.0 wt. %, 5.0 wt. %, 7.0 wt. %, 8.25 wt. %, including every number and/or fraction therebetween, based on the total weight of the sunscreen composition. For example, a sunscreen composition may include *Zea Mays* Starch (and) Polyvinyl Alcohol (and) Glycerin in an amount s about 5.0 wt. %, based on the total weight of the sunscreen composition.

Sunscreen Format(s)

A sunscreen composition may include one or more formulation formats such as, without limitation, an emulsion (O/W, W/O, etc.), a gel, an oil, an anhydrous composition, a base, or combinations thereof. Additionally or alternatively, a sunscreen composition may include one or more application formats such as, without limitation, a lotion, a cream, a spray, a stick, a mouse, a foam, a powder, an ointment, a milk, or combinations thereof. Such formats may initially or finally be substantially aqueous or substantially anhydrous. For example, a substantially anhydrous base may be used in an aqueous emulsion to form a lotion or a cream. Similarly, ingredients and use levels to make such formats may be readily adjusted and mixed in a single phase or in multiple phases to provide a desired commercial sunscreen product. Thus, for example, water content, alcohol content, oil content, emulsifiers, foaming agents, gelling agents, etc., may be included, omitted, adjusted, or mixed in a single phase or in multiple phases to provide a commercial sunscreen product that accounts for cost, aesthetics, and/or product performance objectives.

Moreover, a sunscreen composition can be filled into any number of bottles, tottles, tubes, packets, etc., having a variety of closing structures, pumps, sprays (i.e., aerosols, bag on valve), amongst others, or combinations thereof. A sunscreen composition may, for example, be formulated as a concentrate with a propellant to provide a continuous aerosol spray commercial product. The propellant generally exists as equilibrium of vapor and liquid and can be either dissolved in or miscible with the composition. Examples of suitable propellants include isobutene, butane, propane, dimethyl ether, methyl ether, or combinations thereof. Ratios of concentrate to propellant can be adjusted to account for cost, aesthetics, and product performance objectives. In one embodiment, the sunscreen composition concentrate and propellant are added to an aerosol container in a ratio of about 90:10 to about 60:40. The aerosol propellant may be present in an amount of about 10 wt. % to about 60 wt. %, based on a total weight of the sunscreen composition (e.g., final composition). A bag-on-valve system may also be used to deliver the sunscreen composition using compressed gas such as air, nitrogen, or carbon dioxide. In another example, the sunscreen composition may be formulated as an aqueous lotion.

EXAMPLE(S)

All equipment was cleaned and sanitized before batching. Ingredients were mixed in as phases and added under heat while mixing on propeller blade or homogenizer. Heating was conducted between about 40° C. and about 60° C. Mixing was conducted between about 600 RPM to about 2500 RPM for a duration between about 1 minute and about 20 minutes. The pH was adjusted to between about 5.5 and about 6.0 until the batch was uniform, and final mixing on sweep blade continued as the batch cooled to room temperature (about 25° C.). Preferably, the carrier and all sunscreen actives were mixed to provide a combination of sunscreen actives at least partly encapsulated by the same carrier structure.

Example Table 2 shows example sunscreen compositions including a sunscreen active and a synergistic combination of a carrier and a film former.

TABLE 2

| Component (INCI) | Function | Approx. wt. % |
|---|---|---|
| Example Main Ingredients | | |
| Octocrylene, Homosalate, Octisalate, Avobenzone | Sunscreen Active | 15.0 |
| *Carthamus Tinctorius* (Safflower) Oleosomes | Carrier | 1.0-15.0 |
| Acrylates/$C_{12-22}$ Alkyl Methacrylate Copolymer (and) Water | Film Former | 0.1-5.0 |
| Example Other Ingredients | | |
| Phenoxyethanol, Chlorphenesin, Caprylyl Glycol, Coco-Caprylate, Dipropylene Glycol Dibenzoate, Glycerin, Ammonium Acryloyldimethyltaurate/VP Copolymer, Xanthan Gum, and/or Sodium Hydroxide | Preservative System, Emollient, Humectant, Additional Film Former, Binder, pH Adjuster | 0.1-10.0 |
| Water | Solvent | Q.S. to 100 |

In vitro data was obtained using a Labsphere Ultraviolet Transmittance Analyzer (Model UV-2000 available from the Solar Light Company, Philadelphia, Pennsylvania). Samples of the sunscreen compositions weighing 2.0 $mg/cm^2$ were transferred by an adjustable pipette and uniformly applied to a Schonberg sand-blast PMMA plate (roughness 6 μm) by finger with a pre-saturated finger cot. After application, the coated plate was air dried for 30 minutes. The sample plate was placed inside the Labsphere Analyzer. Irradiation took place at 4 randomly selected points. The readings were recorded by the analyzer and the calculation of the SPF and UVAFP values were based on the following equation:

$$SPF = \frac{\int_{280\,nm}^{400\,nm} E_\lambda \cdot S_\lambda \cdot d\lambda}{\int_{280\,nm}^{400\,nm} E_\lambda \cdot S_\lambda \cdot T_\lambda \cdot d\lambda}$$

with built-in software: UV-2000 application Version 1.1.0.0, wherein $E_\lambda$ is the Commission Internationale de l'Eclairage (CIE) erythemal spectral effectiveness, $S_\lambda$ is designated as the solar spectral irradiance, and TA is the spectral transmittance of the sample as measured on the UV-2000. An average of four readings was recorded as the in-vitro SPF value.

Referring to FIG. 1, the SPF values for sunscreen compositions with relatively low amounts of sunscreen actives (e.g., about 15.0 wt. %) were evaluated in vitro. Reference Example 1 had acrylates/$C_{12-22}$ alkyl methacrylate copolymer (and) water in the concentration range shown in Table 2, with water replacing the oleosomes omitted, and yielded an SPF of about 13. Reference Example 2 had *Carthamus Tinctorius* (Safflower) Oleosomes and acrylates/$C_{12-22}$ alkyl methacrylate copolymer (and) water in the concentration ranges shown in Table 2, and yielded an SPF of about 15. The results, therefore, suggested against using the combination of these specific types of ingredients in vivo, since the SPF from Reference Example 1 with the acrylic film former alone was comparable to the SPF from Reference Example 2 having the oleosomes and the acrylic film former. The results further suggested against using the combination of these specific types of ingredients with the sunscreen actives at the concentration levels shown to achieve relatively high SPF values (e.g., ≥50) in vivo.

Additional formulations tested were similar to Reference Examples 1-2 (acrylates/$C_{12-22}$ alkyl methacrylate copolymer (and) water with or without *Carthamus Tinctorius* (Safflower) Oleosomes) except that glycerin and xanthan gum levels were halved, diisopropyl adipate was substituted for coco-caprylate at a 1:1 ratio, and modified tapioca starch was added. In the formulation with the film former polymer and the oleosomes, in vitro SPF was 13.23±0.91. In the formulation with the film former polymer alone, in vitro SPF of was 13.16±1.58. These results, therefore, confirmed the belief that the combination of these types of ingredients would not be beneficial in vivo, and that the combination of these types of ingredients with the sunscreen actives at the concentration levels shown in Table 2 would not achieve relatively high SPF values (e.g., ≥50) in vivo.

The SPF of sunscreen compositions were evaluated under "static" conditions (no water immersion) according to method defined in Final Monograph—Code of Federal Regulations Title 21 CFR 201.327.(i), "SPF Test Procedure, Sunscreen Drug Products for Over-the-Counter Human Use", Federal Register, Vol. 76, No. 117, Jun. 17, 2011. The SPF of the reference sunscreen and the examples was determined based on the following equation:

$$SPFi = \frac{MED(\text{protected skin})}{MED(\text{unprotected skin})} = \frac{MEDp}{MEDu}$$

The study was conducted in a double-blinded manner—neither the test subjects nor the designated staff members of the test facility who evaluated the MED responses knew which sunscreen formulation was applied to which site or what doses of UV radiation were administered. The test method was validated using the "control" sunscreen consisting of a 7% Padimate-O/3% Oxybenzone SPF Standard.

Figure 2:
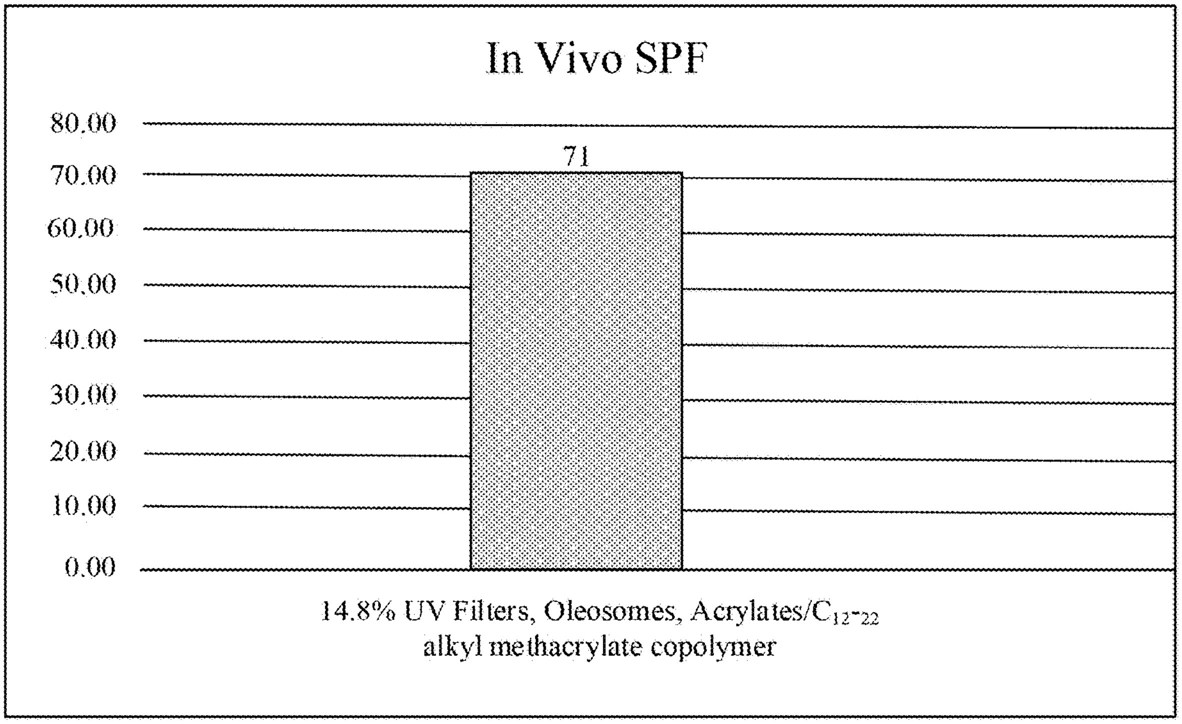
FIG. 2 is a graph showing unexpected enhanced photoprotection from a sunscreen composition including a sunscreen active and a synergistic combination of a carrier and a film former polymer in vivo according to embodiments.

Turning now to FIG. 2, an example sunscreen composition (Example 1) was formulated with a film former selected from $C_{1-30}$ alkyl (meth)acrylates copolymer and a carrier selected from natural-based micelles (oleosomes) in the concentration range shown in Table 2. Example 1 unexpectedly and surprisingly provided a mean SPF greater than 70 at relatively lower concentrations of sunscreen active in vivo. Indeed, the sunscreen actives were more than halved compared to traditional amounts used for an SPF of 50 or greater. Moreover, a boost in SPF was unexpectedly and surprisingly observed for UV filters at least partly and preferably mostly encapsulated or carried by oleosomes together with a film former selected from $C_{1-30}$ alkyl (meth) acrylates copolymer. Additionally, Example 1 shows a relatively lower amount of carrier (e.g., oleosome dispersion≤about 10 wt. %) and/or of acrylic acid film former (e.g., film form dispersion≤about 2.5 wt. %) may be utilized.

A further evaluation was conducted to determine whether similar unexpected and surprising in vivo photoprotection could be achieved despite in vitro results. The additional formulation tested was the same as the previously tested additional formulation (similar to Reference Examples 2 having acrylates/$C_{12-22}$ alkyl methacrylate copolymer (and) water with *Carthamus Tinctorius* (Safflower) Oleosomes, glycerin and xanthan gum levels lowered by half, diisopropyl adipate substituted for coco-caprylate at a 1:1 ratio, and 2% of modified tapioca starch). The in vivo SPF of the additional formulation was 57.11 (VWR) and 37.67 (static). These results, therefore, confirmed the unexpected and surprising results that the combination of these types of ingredients would be beneficial in vivo, and that the combination of these types of ingredients with the sunscreen actives at the concentration levels shown in Table 2 would achieve relatively high SPF values (e.g., ≥50) in vivo.

Thus, example formulations may minimize the cost of a sunscreen composition and/or may minimize technical challenges related to its application or performance. For example, relatively lower temperatures may be used to produce a sunscreen composition that includes a relatively lower amount of ingredients such as sunscreen actives. Without being bound to any theory, example formulations may further address challenges such as oleosome collapse.

ADDITIONAL NOTES AND EXAMPLE(S)

It is understood that the examples above include aspects of non-limiting embodiments, and that listed ingredients or respective levels or ratios may be modified based on various formulation criteria such as, without limitation, format, photoprotection, sensory profile, water resistance, diffusion profile, solubility profile, and so on.

For example, the film former listed in Table 2 may be omitted, replaced, or adjusted in concentration. In one example, the film former may be replaced by or optionally include other acrylates copolymers such as, without limitation, $C_{1-30}$ alkyl (meth)acrylate copolymers selected from, e.g., $C_{6-14}$ perfluoroalkylethyl acrylate/HEMA copolymer, $C_{8-22}$ alkyl C acrylates/methacrylic acid crosspolymer, $C_{2-16}$ alkyl PEG-7 methacrylate/perfluorohexylethyl methacrylate copolymer, acrylates/$C_{5-8}$ alkyl acrylate copolymer, or combinations thereof. Additionally or alternatively, embodiments may include at least one cross polymer as a rheology modifier agent and require at least one film former polymer having a molecular weight of 1,500,000 Daltons or less, or optionally be free of a rheology modifier agent such as acrylates/$C_{10-30}$ alkyl acrylate cross polymer. In this regard, a total amount of film former polymer may be present in an amount of about 0.1 wt. % to about 5.0 wt. %, based on the total weight of the sunscreen composition. For example, one or more film former polymers such as those listed may be present in an amount of 0.08 wt. %, 0.9 wt. %, 1.0 wt. %, 2.5 wt. %, 5.0 wt. %, 6.0 wt. %, including every number and/or fraction therebetween, based on the total weight of the sunscreen composition.

Additionally or alternatively, any or all of the sunscreen actives listed in Table 2 may be omitted, replaced, or adjusted in concentration to provide varying levels of photoprotection, solubility, and so on. For example, a sunscreen active may be selected from a p-aminobenzoic acid, a benzophenone, a camphor, a cinnamate, a dibenzoylmethane, a salicylate, an imidazole, a triazole, a triazine, a triazole, triazone, a metal oxide, or combinations thereof. Thus, for example, the sunscreen composition may include: p-aminobenzoic acids such as p-aminobenzoic acid (CAS #: 150-13-0), p-aminobenzoic acid, monoglyceryl ester (CAS #: 136-44-7), p-aminobenzoic acid, octyl dimethyl ester (padimate-0, CAS #: 21245-02-3), p-aminobenzoic acid, ethyl dihydroxypropyl (roxadimate, CAS #: 58882-17-0), p-aminobenzoic acid, 2,4-dihydroxy-N-(3-hydroxypropyl)-3,3-dimethylbutanamide ester, p-aminobenzoic acid, PEG-25 (CAS #: 116242-27-4); anthranilates such as menthyl anthranilate (CAS #: 134-09-8); benzophenones such as benzophenone (CAS #: 119-61-9), 2,4-dihydroxybenzophenone (benzophenone-1, CAS #: 131-56-6), 2,2',4,4'-tetrahydroxybenzophenone (benzophenone-2, CAS #: 131-55-5), 2-hydroxy-4-methoxybenzophenone (benzophenone-3, oxybenzone, CAS #: 131-57-7), 2-hydroxy-4-methoxybenzophenone-5-sulfonic acid (benzophenone-4, sulisobenzone, CAS #: 4065-45-6), 2-hydroxy-4-methoxybenzophenone-5-sulfonic acid, monosodium salt (benzophenone-5, CAS #: 6628-37-1), 2,2'-dihydroxy-4,4'-dimethoxybenzophenone (benzophenone-6, CAS #: 131-54-4), 5-chloro-2-hydroxybenzophenone (benzophenone-7, CAS #: 85-19-8), 2,2'-dihydroxy-4-methoxybenzophenone (benzophenone-8, dioxybenzone, CAS #: 131-53-3), 2,2'-dihydroxy-4,4'-dimethoxybenzophenone-5,5'-disulfonic acid sodium salt (benzophenone-9, CAS #: 76656-36-5), 2-hydroxy-4-methoxy-4'-methyl-benzophenone (benzophenone-10, Mexenone, CAS #: 1641-17-4), bis(2,4-dihydroxyphenyl)methanone (benzophenone-11, CAS #: 1341-54-4), 2-hydroxy-4-(octyloxy)benzophenone (benzophenone-12, octabenzone, CAS #: 1843-05-6), 2,2'-dihydroxy-4-methoxybenzophenone (dioxybenzone, CAS #: 131-53-3), 2-hydroxy-4-methoxybenzophenone (oxybenzone, CAS #: 131-57-7), 2-hydroxy-4-methoxybenzophenone-5-sulphonic acid (sulisobenzone, CAS #: 4065-45-6), hexyl 2-(4-(diethylamino)-2-hydroxybenzoyl)benzoate (CAS #: 302776-68-7); camphors such as benzylidene camphor sulfonic acid (CAS #: 56039-58-8), 3-benzylidene camphor (CAS #: 15087-24-8), polyacrylamidomethyl benzylidene camphor (CAS #: 113783-61-2), terephthalylidene dicamphor sulfonic acid (CAS #: 90457-82-2), 3-(4-methylbenzyliden)camphor (CAS #: 36861-47-9), camphor benzalkonium methosulfate (CAS #: 52793-97-2), bornelone (CAS #: 2226-11-1); cinnamates such as ethyl cinnamate (CAS #: 103-36-6), 2-ethoxyethyl-p-methoxycinnamate (cinoxate, CAS #: 104-28-9), isoamyl p-methoxycinnamate (CAS #: 71617-10-2), diisopropyl methyl cinnamate (CAS #: 32580-71-5), 2-ethylhexyl alpha-cyano-beta-phenylcinnamate (octocrylene, CAS #: 6197-30-4), diethanolamine methoxycinnamate (CAS #: 56265-46-4), isopropyl methoxycinnamate (CAS #: 5466-76-2), isoamyl p-methoxycinnamate (CAS #: 71617-10-2), glyceryl octanoate dimethoxycinnamate, ethyl diisopropylcinnamate (CAS #: 32580-72-6), ethyl methoxycinnamate (CAS #: 99880-64-5), octyl methoxycinnamate (octinoxate, CAS #: 5466-77-3); dibenzoylmethanes such as dibenzoylmethane (CAS #: 120-46-7), isopropyl dibenzoylmethane (eusolex, CAS #: 63250-25-9), 4-tert-Butyl-4'-methoxy-dibenzoylmethane (avobenzone, CAS #: 70356-09-1); salicylates such as 3,3,5-trimethylcyclohexyl salicylate (homosalate, CAS #: 118-56-9), benzyl salicylate (CAS #: 118-58-1), octyl salicylate (octisalate, CAS #: 118-60-5), 2-hydroxyethyl salicylate (CAS #: 87-28-5), menthyl salicylate (CAS #: 89-46-3), isopropylbenzyl salicylate (CAS #: 94134-93-7); imidazoles such as phenylbenzimidazole, phenylbenzimidazol-5-sulfonic acid (CAS #: 27503-81-7), phenylbenzimidazole tea sulfonate (CAS #: 73705-00-7), urocanic acid [4-imidazoleacrylic acid, CAS #: 104-98-3], ethyl urocanate (CAS #: 27538-35-8), bisymidazylate (CAS #: 180898-37-7), sodium phenylbenzimidazole sulfonate (CAS #: 5997-53-5); triazines such as bis(ethylhexyloxyphenol methoxyphenol) triazine (bemotrizinol, CAS #: 187393-00-6); triazoles such as 2-(2-hydroxy-5-methyl-phenyl)benzotriazole (drometrizole, CAS #: 2440-22-4); triazones such as bis-ethylhexyloxyphenol methoxyphenyl triazine (iscotrizinol, CAS #: 154702-15-5), ethylhexyl triazone (CAS #: 88122-99-0); petrolatum jelly (CAS #: 8009-03-8), acrylates such as diurethane dimethacrylate (CAS #: 103597-45-1), ethyl 2-cyano-3,3-diphenylacrylate (etocrilene, CAS #: 5232-99-5); siloxanes such as drometrizole trisiloxane (CAS #: 155633-54-8); or combinations thereof.

In one example, the sunscreen composition may only include one or more organic sunscreen actives. For example, embodiments may include a sunscreen active that protects against UVA radiation such as avobenzone (e.g., Parasol® 1789), diethylamino hydroxybenzoyl hexyl benzoate (e.g., Uvinul® A Plus), terephthalylidene dicamphor sulfonic acid, bis-disulizole disodium, disodium phenyl dibenzimidazole tetrasulfonate, bis-diethylamino hydroxybenzoyl benzoate, bis-benzoxazolylphenyl ethylhexylamino triazine, or combinations thereof. Additionally or alternatively, embodiments may include a sunscreen active that protects against UVB radiation such as octocrylene, octinoxate, octisalate, homosalate, ensulizole, ethylhexyl triazone (e.g., Uyinul® T150), enzacamene, amiloxate, bemotrizinol (e.g., Uvasorb® HEB), benzylidene malonate polysiloxane, padimate-O, trolamine salicylate, cinoxate, PABA, or combinations thereof. Additionally or alternatively, embodiments may include a sunscreen filter that protects against UVA and UVB radiation such as oxybenzone, meradimate, titanium dioxide, zinc oxide, bis-octrizole, bis-ethylhexyloxyphenol methoxyphenyl triazine (Tinosorb® S), drometrizole trisiloxane, sulisobenzone, dioxybenzone, or combinations thereof. Additionally or alternatively, embodiments may exclude benzophenone-3, octyl methoxycinnamate, 2-ethylhexyl-2-cyano-3,3-diphenylacrylate, 3,3,5-trimethylcyclohexyl salicylate, 2-ethylhexyl salicylate, or combinations thereof.

A total amount of sunscreen active may, for example, be present in an amount of about 1.0 wt. % to less than 30.0 wt. %, based on the total weight of the sunscreen composition. For example, one or more sunscreen actives such as those listed may be present in an amount of 0.8 wt. %, 1.0 wt. %, 2.0 wt. %, 3.0 wt. %, 4.0 wt. %, 5.0 wt. %, 6.0 wt. %, 7.0 wt. %, 8.0 wt. %, 9.0 wt. %, 10.0 wt. %, 15.0 wt. %, 20.0 wt. %, 25.0 wt. %, 29.9 wt. %, including every number and/or fraction therebetween, based on the total weight of the sunscreen composition.

Additionally or alternatively, the carrier listed in Table 2 having an amphiphile monolayer to at least partly encapsulate the sunscreen active may be omitted, replaced, or adjusted in concentration. For example, sunscreen compositions may include Oleosomes selected from *Carthamus Tinctorius* oleosomes and/or *Prunus Amygdalus Dulcis* oleosomes such as, without limitation, *Carthamus Tinctorius* (Safflower) Oleosomes (and) Water, *Carthamus Tinctorius* (Safflower) Oleosomes (and) Glycerin (and) Water, and/or *Prunus Amygdalus Dulcis* (Sweet Almond) Oleosomes (and) Glycerin (and) Water, or combinations thereof. A total amount of carrier may be present in an amount of about 1.0 wt. % to about 15.0 wt. %, based on the total weight of the sunscreen composition. For example, one or more carriers such as those listed may be present in an amount of 0.8 wt. %, 1.0 wt. %, 5.0 wt. %, 10.0 wt. %, 15.0 wt. %, 18.0 wt. %, including every number and/or fraction therebetween, based on the total weight of the sunscreen composition.

Similarly, any or all of the other ingredients listed in Table 2 may be omitted, replaced, or adjusted in concentration. For example, a sunscreen composition may include other ingredients such as, without limitation, added water, additional film formers, cosmetically acceptable carriers, oils, sterols, amino acids, moisturizers, powders, colorants, pigments, dyes, pH adjusters, fragrances, cosmetic active ingredients, vitamins, preservatives, preservative boosters, foaming agents, chelating agents, cleansers, essential fatty acids, sphingolipids, self-tanning compounds, fillers, emulsifiers, antioxidants, surfactants, additional film formers, chelating agents, gelling agents, thickeners, emollients, humectants, minerals, viscosity and/or rheology modifiers, keratolytics, retinoids, hormonal compounds, alpha-keto acids, anti-mycobacterial agents, anti-fungal agents, anti-microbials, anti-virals, analgesics, anti-allergenic agents, H1 or H2 antihistamines, anti-inflammatory agents, anti-irritants, anti-neoplastics, immune system boosting agents, immune system suppressing agents, anti-acne agents, anesthetics, antiseptics, insect repellents, skin cooling compounds, skin protectants, skin penetration enhancers, exfoliants, lubricants, staining agents, depigmenting agents, hypopigmenting agents, stabilizers, pharmaceutical agents, photostabilizing agents, spherical powders, extracts (fruit, flower, plant), absorbents, salicylic acid, alpha and beta hydroxy acids, retinol and its derivatives, or combinations thereof.

Accordingly, while the present disclosure has been particularly described, in conjunction with specific preferred embodiments, it is evident that many alternatives, modifications, and variations will be apparent to those skilled in the art in light of the foregoing description. It is therefore contemplated that the appended claims will embrace any such alternatives, modifications, and variations as falling within the true scope and spirit of the present disclosure.

What is claimed is:

1. A sunscreen composition comprising:

a sunscreen active including an organic sunscreen active, wherein the organic sunscreen active is present in an amount of greater than zero to less than or equal to 15.0 wt. %, based on the total weight of the sunscreen composition;

a carrier selected from a micelle, wherein the micelle comprises an oleosome, wherein the oleosome is present in an amount of 0.8 wt. % to less than or equal to 10.0 wt. %, based on the total weight of the sunscreen composition; and an acrylic film former polymer selected from $C_{1-30}$ alkyl (meth)acrylates copolymer, wherein the $C_{1-30}$ alkyl (meth)acrylates copolymer comprises acrylates/$C_{12-22}$ alkyl methacrylate copolymer, wherein the acrylates/$C_{12-22}$ alkyl methacrylate copolymer is present in an amount of greater than zero to less than or equal to 2.5 wt. %, based on the total weight of the sunscreen composition; and wherein the sunscreen composition has a Sun Protection Factor (SPF) greater than or equal to 50.

2. The sunscreen composition of claim 1, wherein the sunscreen active comprises avobenzone, diethylamino hydroxybenzoyl hexyl benzoate, octocrylene, octinoxate, octisalate, homosalate, ethylhexyl triazone, bemotrizinol, bis-ethylhexyloxyphenol methoxyphenyl triazine, titanium dioxide, zinc oxide, or combinations thereof.

3. The sunscreen composition of claim 1, wherein the sunscreen active is selected from the group consisting of organic sunscreen actives.

4. The sunscreen composition of claim 1, wherein the oleosome is selected from *Carthamus Tinctorius* oleosomes, *Prunus Amygdalus Dulcis* oleosomes, or combinations thereof.

5. The sunscreen composition of claim 4, wherein the oleosome is selected from *Carthamus Tinctorius* oleosomes.

6. The sunscreen composition of claim 1, wherein the oleosome is present in an amount of 1.0 wt. % to less than or equal to 10.0 wt. %, based on the total weight of the sunscreen composition.

7. The sunscreen composition of claim 1, wherein the $C_{1-30}$ alkyl (meth)acrylates copolymer has a molecular weight of 1,000,000 Daltons or less.

8. The sunscreen composition of claim 1, further including one or more boosters, cosmetically acceptable carriers, oils, sterols, amino acids, moisturizers, powders, colorants, pigments, dyes, pH adjusters, fragrances, cosmetic active ingredients, vitamins, preservatives, preservative boosters, foaming agents, chelating agents, cleansers, essential fatty acids, sphingolipids, self-tanning compounds, fillers, emulsifiers, antioxidants, surfactants, additional film formers, chelating agents, gelling agents, thickeners, emollients, humectants, minerals, viscosity and/or rheology modifiers, keratolytics, retinoids, hormonal compounds, alpha-keto acids, anti-mycobacterial agents, anti-fungal agents, anti-microbials, anti-virals, analgesics, anti-allergenic agents, H1 or H2 antihistamines, anti-inflammatory agents, anti-irritants, anti-neoplastics, immune system boosting agents, immune system suppressing agents, anti-acne agents, anesthetics, antiseptics, insect repellents, skin cooling compounds, skin protectants, skin penetration enhancers, exfoliants, lubricants, staining agents, depigmenting agents, hypopigmenting agents, stabilizers, pharmaceutical agents, photostabilizing agents, spherical powders, extracts, absorbents, salicylic acid, alpha and beta hydroxy acids, retinol and its derivatives, or combinations thereof.

9. The sunscreen composition of claim 1, further including a booster.

10. The sunscreen composition of claim 9, wherein the booster comprises a carbohydrate selected from maize starch, potato starch, wheat starch, rice starch, cassava starch, tapioca starch, barley starch, or combinations thereof.

11. The sunscreen composition of claim 10, wherein the booster is present in an amount of greater than zero to less than or equal to 7.5 wt. %, based on the total weight of the sunscreen composition.

12. The sunscreen composition of claim 10, wherein the booster comprises *Zea* Maize starch.

13. The sunscreen composition of claim 1, wherein the sunscreen composition is in the form of a lotion or a cream.

14. A sunscreen method to protect a keratinous surface from ultraviolet (UV) radiation comprising contacting the keratinous surface with the sunscreen composition of claim 1.

15. A consumer packaged product comprising the sunscreen composition of claim 1.

16. The sunscreen composition of claim 1, wherein the sunscreen active excludes ethylhexyl methoxycinnamate (octinoxate).

17. The sunscreen composition of claim 16, wherein the sunscreen active includes a salicylate.

18. The sunscreen composition of claim 1, wherein the sunscreen composition has an in vivo SPF greater than or equal to 50.

* * * * *